United States Patent
Wei et al.

(10) Patent No.: US 10,258,231 B2
(45) Date of Patent: Apr. 16, 2019

(54) METHODS AND APPARATUS FOR RETINA BLOOD VESSEL ASSESSMENT WITH OCT ANGIOGRAPHY

(71) Applicant: OPTOVUE, INC., Fremont, CA (US)

(72) Inventors: Jay Wei, Fremont, CA (US); Tony H. Ko, Cupertino, CA (US); Yi-Sing Hsiao, Fremont, CA (US); Ben Jang, Cupertino, CA (US); Richard Rosen, New York, NY (US)

(73) Assignee: OPTOVUE, INC., Fremont, CA (US)

( * ) Notice: Subject to any disclaimer, the term of this patent is extended or adjusted under 35 U.S.C. 154(b) by 72 days.

(21) Appl. No.: 14/985,197

(22) Filed: Dec. 30, 2015

(65) Prior Publication Data

US 2016/0183786 A1   Jun. 30, 2016

Related U.S. Application Data (60) Provisional application No. 62/098,230, filed on Dec. 30, 2014.

(51) Int. Cl.
```
A61B 3/12      (2006.01)
A61B 3/10      (2006.01)
A61B 3/00      (2006.01)
G06T 7/00      (2017.01)
G06T 7/12      (2017.01)
```

(52) U.S. Cl.
CPC .......... *A61B 3/1233* (2013.01); *A61B 3/0025* (2013.01); *A61B 3/0041* (2013.01); *A61B 3/102* (2013.01); *G06T 7/0014* (2013.01); *G06T 7/12* (2017.01); *G06T 2200/24* (2013.01); *G06T 2207/10101* (2013.01); *G06T 2207/20044* (2013.01); *G06T 2207/30041* (2013.01); *G06T 2207/30104* (2013.01); *G06T 2207/30172* (2013.01)

(58) Field of Classification Search
CPC ... A61B 3/1233; A61B 3/0041; A61B 3/0025; A61B 3/102; G06T 7/12; G06T 7/0014; G06T 2200/24; G06T 2207/20044; G06T 2207/30104; G06T 2207/30172; G06T 2207/10101; G06T 2207/30041
USPC .......................................................... 351/205
See application file for complete search history.

(56) References Cited

U.S. PATENT DOCUMENTS

| | | | |
|---|---|---|---|
| 7,505,142 B2 | 3/2009 | Knighton et al. | |
| 2013/0301008 A1* | 11/2013 | Srivastava | G01B 9/02083 351/246 |
| 2014/0073917 A1 | 3/2014 | Huang et al. | |

OTHER PUBLICATIONS

David Huang, MD, PhD, Functional & Structural OCT in Glaucoma; Japan Glaucoma Society Meeting, Tokyo; Sep. 21-23, 2013; http://www.aigstudy.net/fileadmin/aigs_upload/docs/StructFunctOCT-Glaucoma-JGS2013.pdf.*

(Continued)

*Primary Examiner* — Jade R Chwasz
*Assistant Examiner* — Rahman Abdur
(74) *Attorney, Agent, or Firm* — Haynes and Boone, LLP (57) ABSTRACT

A method of processing a 3D OCT dataset is present. A method according to some embodiments of the present invention includes obtaining an OCT data from the 3D OCT dataset; obtaining an OCTA data from the 3D OCT dataset; performing segmentation for at least one boundary on the OCT data; processing the OCTA data in a region of interest to create at least one image representation by assigning a value to each pixel of each of the image representation; and displaying at least one image representation.

19 Claims, 9 Drawing Sheets

(56) References Cited

OTHER PUBLICATIONS

Huang, D. "Functional & Structural OCT in Glaucoma" Japan Glaucoma Society Meeting, Tokyo, Japan, Sep. 2013. [Retrieved on Feb. 14, 2016]. Retrieved from Internet: <http://www.aigstudy.net/fileadmin/aigs_upload/docs/StructFunctOCT-Glaucoma-JGS2013.pdf> entire document.
PCT International Search Report dated Feb. 26, 2016 for PCT/US2015/068194. pp. 1-2.
PCT Written Opinion dated Feb. 26, 2016 for PCT/US2015/068194. pp. 1-4.

* cited by examiner

METHODS AND APPARATUS FOR RETINA BLOOD VESSEL ASSESSMENT WITH OCT ANGIOGRAPHY

RELATED APPLICATIONS

This disclosure claims priority to U.S. Provisional Patent Application 62/098,230 by Jay Wei, Tony Ko, Yi-Sing Hsiao, Ben Jang, and Richard Rosen, entitled "Methods and Apparatus for Retina BloodVessel Assessment with OCT Angiography," filed on Dec. 30, 2014, which is herein incorporated by reference in its entirety.

TECHNICAL FIELD

Embodiments of the present invention relate generally to the field of optical coherence tomography angiography and, specifically, embodiments of the present invention relate generally to methods and systems for measuring blood vessel and capillary flow and non-flow area and density.

DISCUSSION OF RELATED ART

In the past several decades, fundus camera had been used to image blood flow in the retina by sensing fluorescence of the dye in the blood vessel used in flourescein angiography (FA) or Indocyanine Green (ICG) techniques. These methods require injection of a contrast agent such as a fluorescent dye into the blood stream. Then the retina is illuminated with light of a proper wavelength to excite the dye and the fluorescence from the dye is detected. However, the dye flows quickly through the blood vessel and will disappear after a short period of time. Further, time sequence imaging is required in these techniques in order to reveal a full picture of the blood vessels using. Also, fluorescence emission is very weak in small vessels, such as the capillaries, and thus it is very difficult to see small vessels using these fluorescence methods. For example, the radial peripapillary capillaries and deep capillaries are difficult to observe using FA techniques.

Additionally, since the FA is based on a fundus imaging method of measurement, it can only show the blood flow in a two-dimensional topographic view. The blood vessel cannot be segmented into different layers for measurement using traditional methods such as FA. Furthermore, the FA approach is invasive with the injection of the dye, no normative database has been established as a reference for blood flow assessment.

Optical Coherence Tomography (OCT) Angiography (OCTA) is a non-invasive vascular image modality by using OCT scanning. It is different from Fluorescent Angiography (FA) and Indocyanine Green (ICG) in that OCTA is an intrinsic motion-enhanced OCT image which does not require injection of dye. The OCT signal contains both phase information and amplitude information. Motion effects using OCTA can be detected either from the phase information (see, for example, Daniel Schwartz et al. [Phase-Variance Optical Coherence Tomography, Ophthalmology, January 2014]), from the amplitude information (see, for example, Yali Jia et al. [Split-spectrum amplitude-decorrelation angiography with optical coherence tomography, Optics Express, February 2012]) or from both the phase and amplitude variance (see, for example, Lin An et al. [High Resolution wide-field imaging of retina and choroidal blood perfusion with optical micro-angiography, J Biomed Opt, March-April 2010]) of OCT signal.

Therefore, methods and apparatus to quantify the retina blood vessels non-invasively with OCTA in a 3D manner and to assess the blood flow are needed.

SUMMARY

In some embodiments of the present invention, a method of processing a 3D OCT dataset is present. A method according to some embodiments of the present invention includes obtaining an OCT data from the 3D OCT dataset; obtaining an OCTA data from the 3D OCT dataset; performing segmentation for at least one boundary on the OCT data; processing the OCTA data in a region of interest to create at least one image representation by assigning a value to each pixel of each of the image representation; and displaying at least one image representation.

These and other embodiments are further discussed below with respect to the following figures.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various changes may be made without departing from the spirit and scope of this description and the claims. In some instances, well-known structures and techniques have not been shown or described in detail in order not to obscure the invention.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

With the OCTA, the blood vessels and capillaries area and density can be measured. The flow area or the non-flow area on the OCTA can be quantified and compared to a relevant normative database to obtain useful clinical information. Furthermore, the vessel density in the flow area can be quantified and compared to a relevant normative database to obtain further useful clinical information. The normative database can be a group of measurement data which have been clinically diagnosed as normal without pathology. The normative database can be further stratified by ethnicity, age, and gender, depending on the clinical application. Methods can be used to show the results of statistical analysis using a subject measurement data in comparison with the data from the relevant normal group in the normative database.

OCT data analysis methods have been disclosed using the retina tissue thinning map and a normative retina thickness map (see, for example, David Huang et al. [Pattern analysis of retina maps for the diagnosis of optic nerve diseases by optical coherence tomography, U.S. Pat. No. 8,474,978 B2], which is herein incorporated by reference in its entirety). Similar analysis methods can be applied to the OCTA data to provide clinically useful information; for example, a focal loss vessel volume can be computed using the vessel density map and normative vessel density map.

Figure 1:
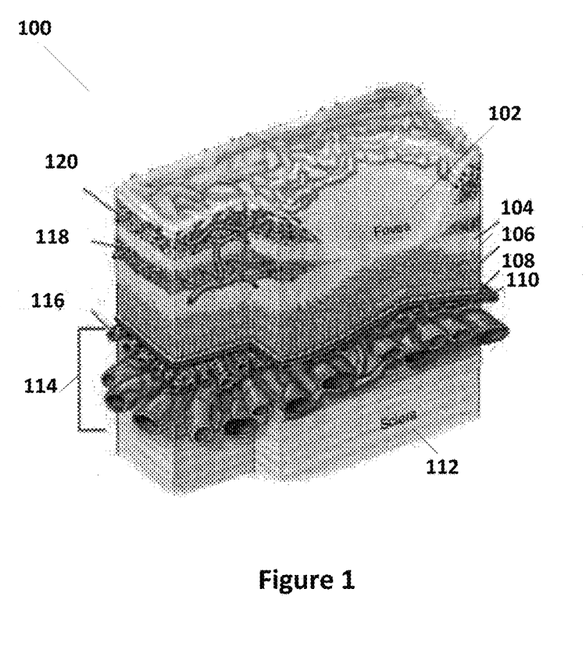
FIG. 1 is a diagram showing the anatomy of the retina and choroidal vasculature and changes that occur at the level of the human fovea.

The retina vascular network 100 is depicted in FIG. 1 as a 3-dimensional structure. FIG. 1 illustrates Fovea 102, Henle's fiber layer 104, photoreceptor layer 106, pigmented epithelium 108, Bruch's membrane 110, and Sclera 112. FIG. 1 further shows choroid arteries 114, choriocapillaris 116, the deep capillary plexus 118, and superficial capillary plexus 120. The vessel changes in different diseases can originate at different layers and migrated into other layers. The capillaries quantity, except the known normal avascular zone in fovea 102 and in the outer retina, is not measured in traditional angiography techniques.

The vessel density of choroid arteries 114, choriocapillaris 116, the deep capillary plexus 118, and superficial capillary plexus 120 can be measured and mapped through several processes, for example to improve the accuracy of the measurement. In some depictions, the vessel density can be color coded or otherwise represented to compose a vessel density color map. For example, the vessel density can be shown in a first color, for example a green color, for high vessel density and a second contrasting color, for example a red color, for low density. Anything between low density and high density can be color coded between the first color and the second color. Other depictions of density variation can also be used.

The non-flow area in the different layers of capillary plexus, for example, superficial capillary plexus 120, deep capillary plexus 120, and choriocapillaries 116, can be outlined from a vessel density map. In the same time, the detected flow area in the normally avascular zone, for example the outer retina of retina structure 100, can be calculated to measure abnormal vessel presence and vessel density in those zones.

Some embodiments of the current invention further disclose methods to quantitatively assess the blood flow status of the retina structure 100 at different layers by comparing to a normative database. In some embodiments, the results of the measured data, when compared to the distribution of the normal group data, can be depicted, for example by color coding, for easy visualization. For example, if the vessel density is larger than 5% of the normal distribution, the area can be coded in a first color, for example green; if the vessel density is between 1% and 5% the area can be coded in a second color, for example yellow; and if the vessel density is less than 1% of the normal distribution, the area can be coded in a third color, for example red. The normative database can be further stratified when it is used to compare to the specific patient's characteristics, such as ethnicity, age, and/or gender. In some embodiments, changes of the vessel density over time can also be displayed as a color coded difference map. The statistically significant trend of changes, in some embodiments, can also be plotted graphically over the time or depicted in other ways.

Figure 10:
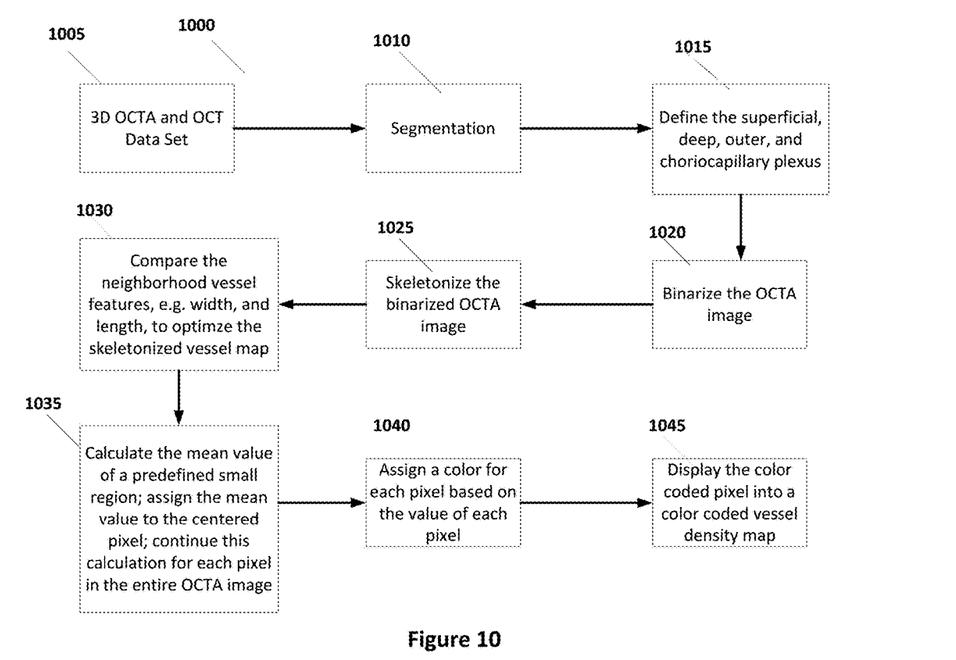
FIG. 10 shows a block diagram illustrating formation of a vessel density map at different layers of the retina according to some embodiments of the present invention.

The OCT angiography image can be formed from a three-dimensional data set according to some embodiments. The 3D data set can contain data from two OCT image modalities, the OCT and OCTA modalities. The principles of how to form an OCT image from an OCT data set and an OCTA image from an OCTA data set have been disclosed in prior publications as discussed above and will not be further discussed herein. FIG. 10, which is discussed in further detail below, illustrates formation of an enface OCTA image, a layer depth resolved OCTA image, and a vessel density map.

Figure 2:
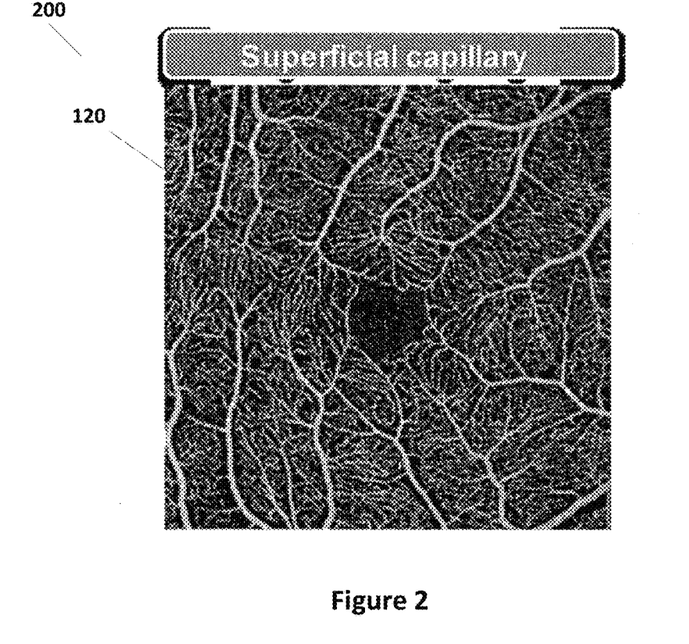
FIG. 2 illustrates an exemplary image of OCT Angiography on Superficial Capilliary Plexus according to some embodiments.
Figure 3:
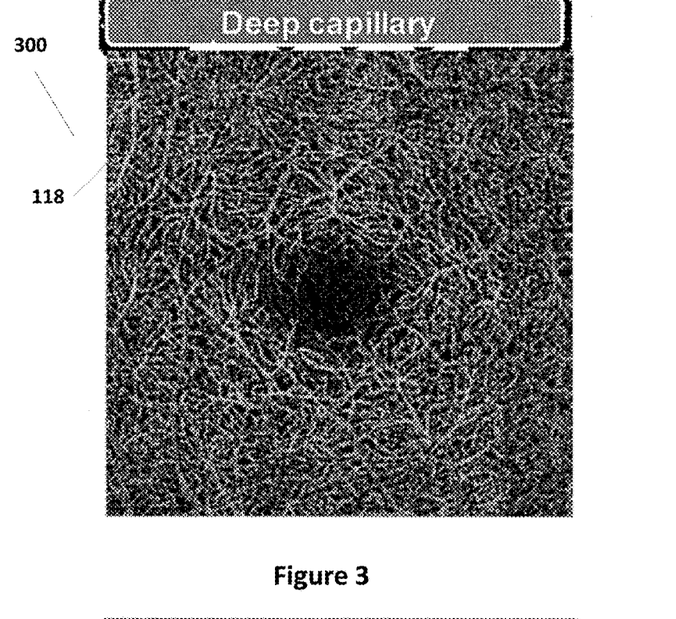
FIG. 3 illustrates an exemplary image of OCT Angiography on Deep Capillary Plexus according to some embodiments.
Figure 4:
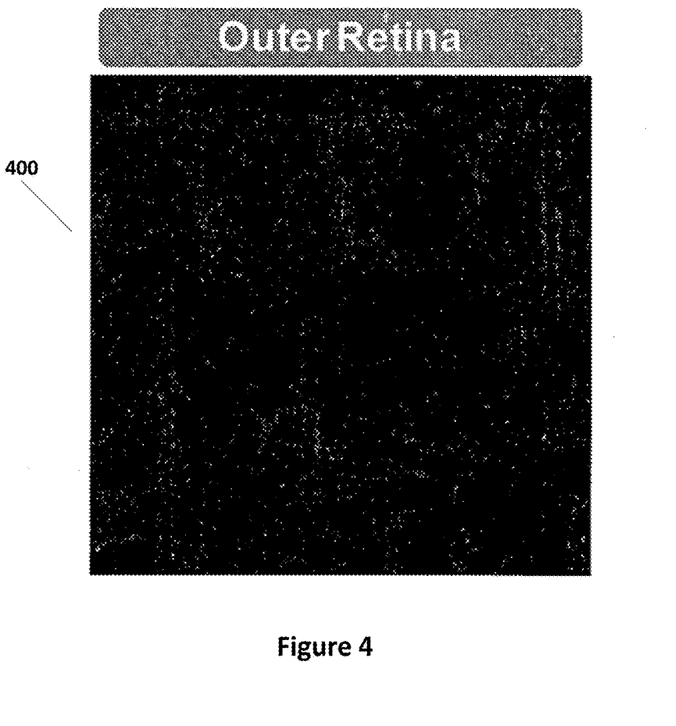
FIG. 4 illustrates an exemplary image of OCT Angiography on Outer Retina Avascular Zone (normal) according to some embodiments.
Figure 5:
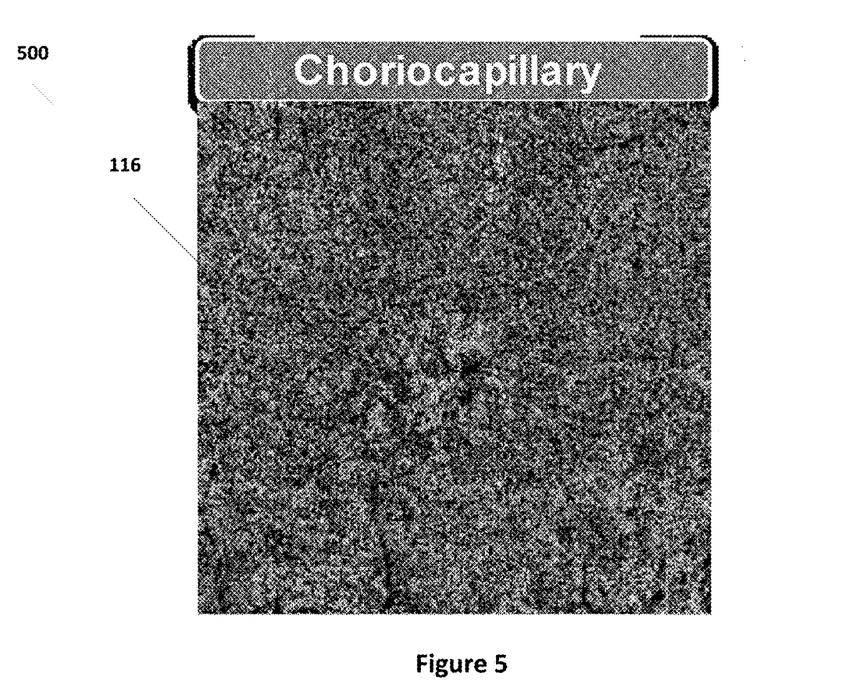
FIG. 5 illustrates an exemplary image of OCT Angiography on Choriocapillary according to some embodiments.

FIGS. 2 through 5 illustrate exemplary image from OCTA data at different layer depth resolution according to some embodiments. FIG. 2 illustrates an image 200 of a layer of superficial capillary 120. FIG. 3 illustrates an image 300 of a layer of deep capillary 118. FIG. 4 illustrates an image 400 of the outer retina. FIG. 5 illustrates an image 500 of a layer of choriocapillary 116.

Figure 6A:
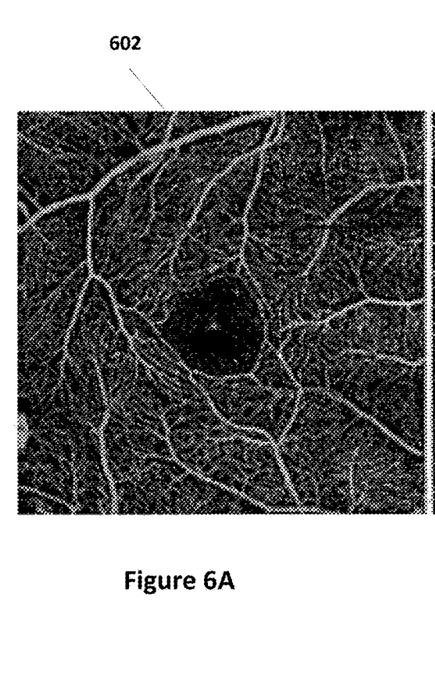
FIG. 6A illustrates an exemplary process from an enface OCTA image to a superficial plexus
Figure 6B:
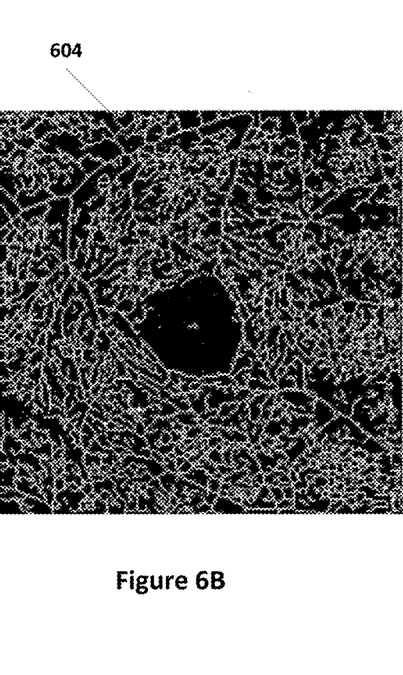
FIG. 6B illustrates an exemplary process from an enface OCTA image to a skeletonized blood vessel image.
Figure 6C:
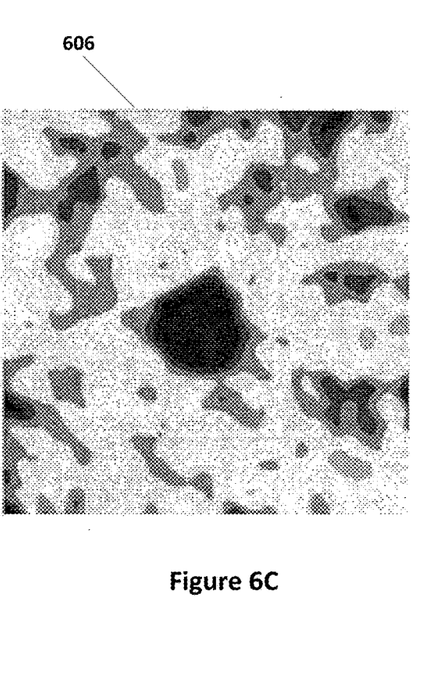
FIG. 6C illustrates an exemplary process from an enface OCTA image to a map of vessel density according to some embodiments.

FIGS. 6A-C further illustrates exemplary results from an enface OCTA image to an enface vessel density map. FIG. 6A illustrates an enface OCTA image 602 of a layer of blood vessels. FIG. 6B illustrates an enface OCTA image 604 of another layer of blood vessels. FIG. 6C illustrates an enface image 606 depicting a vessel density map. In some embodiments of the present invention, an average vessel density value can be calculated in a pre-defined region of the vessel density map.

Figure 7:
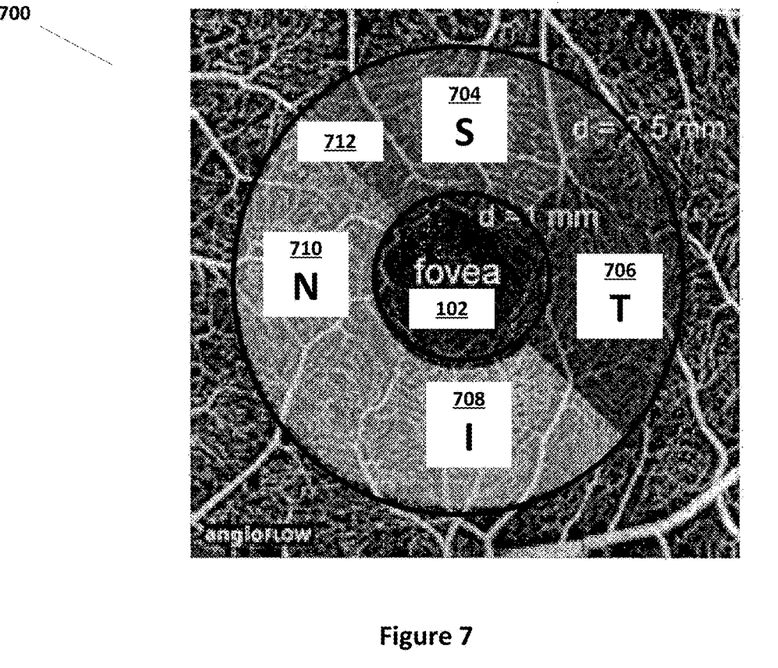
FIG. 7 illustrates an exemplary image of measurements in sectors according to some embodiments.

FIG. 7 illustrates an image 700 with a ring shape parafoveal 712 region with 5 different sectors—the fovea region 102, superior region S 704, tempo region T 706, inferior region I 708 and nasal region N 710—centered on the fovea 102 according to some embodiments. In many exemplary examples, the fovea region can have a diameter of 1 mm and parafoveal region 712 is within 1 mm to 2.5 mm diameter concentric rings. However, these regions can vary in size by 10% or more.

Figure 8:
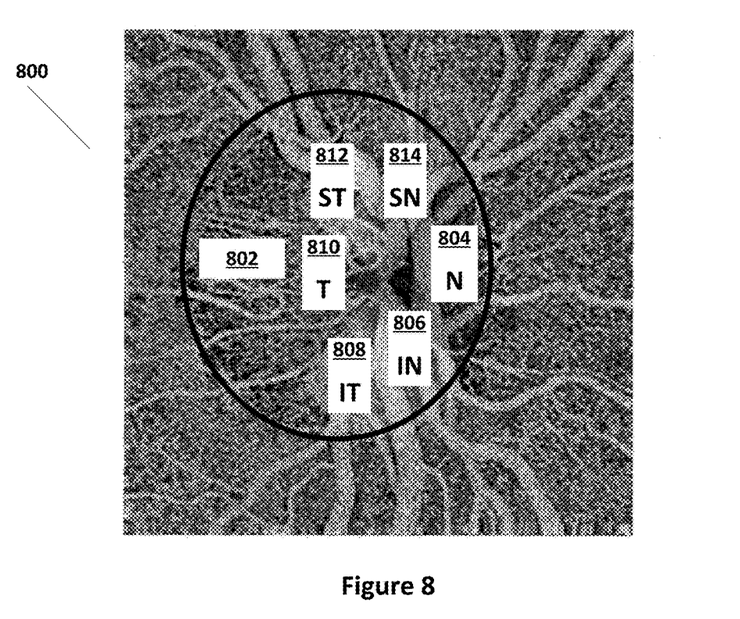
FIG. 8 illustrates an exemplary image of measurements in sectors inside the optic disc according to some embodiments.

FIG. 8 illustrates an exemplary image 800 of measurements in sectors inside optic disc 802 for superior nasal SN 814, nasal N 804, inferior nasal IN 806, inferior tempo IT, 808, tempo T 810, and superior tempo ST 812 according to some embodiments. The ellipse outlines the optic disc boundary of optic disk 802. As illustrated in FIG. 8, the elliptical shape region outlining the optic disc boundary of optic disk 802 has six (6) sectors centered within the optic disc 802. In some embodiments, the six sectors are divided based on the Garway-Heath map (see Ophthalmology: 2000; vol. 107, pp. 1809-1815).

Figure 9A:
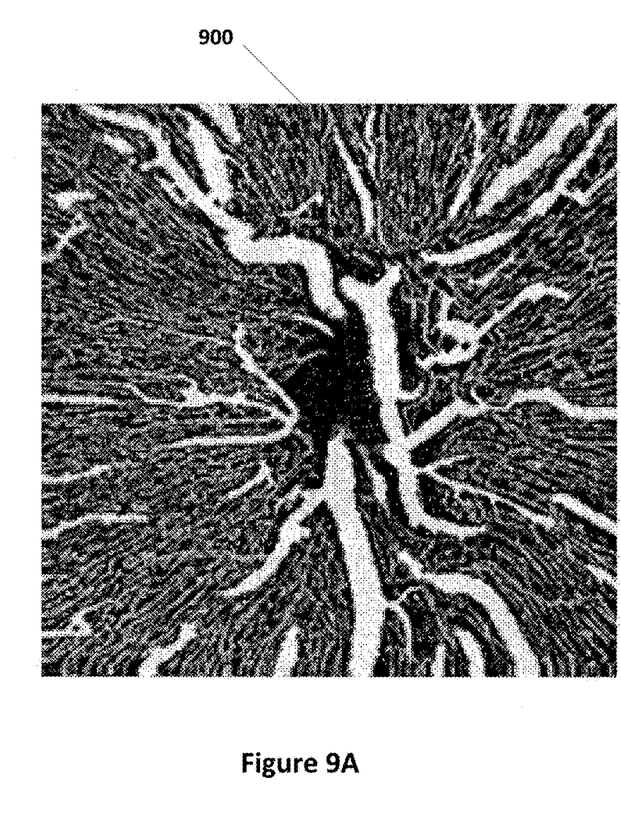
FIGS. 9A and 9B illustrate an exemplary image of measurements in radial peripapillary capillaries (RPC) according to some embodiments.
Figure 9B:
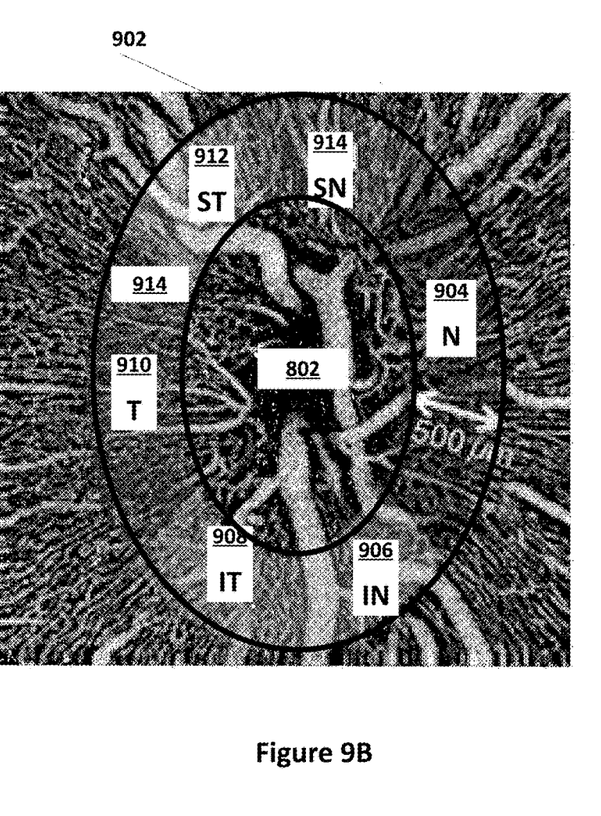

FIG. 9A illustrates an expanded image 900 of optical disk 802 as illustrated in FIG. 8. FIG. 9B illustrates an exemplary radial peripapillary capillary (RPC) density image 902 calculated in a six (6)-sector ring shape region 904—SN 914, N 904, IN 906, IT 908, T 910, and ST 912—around the optic disc 802. The large vessels in and around the optic disc 802, as shown in FIG. 9A, can be identified and removed from the capillary density calculation to improve the accuracy.

Figure 13:
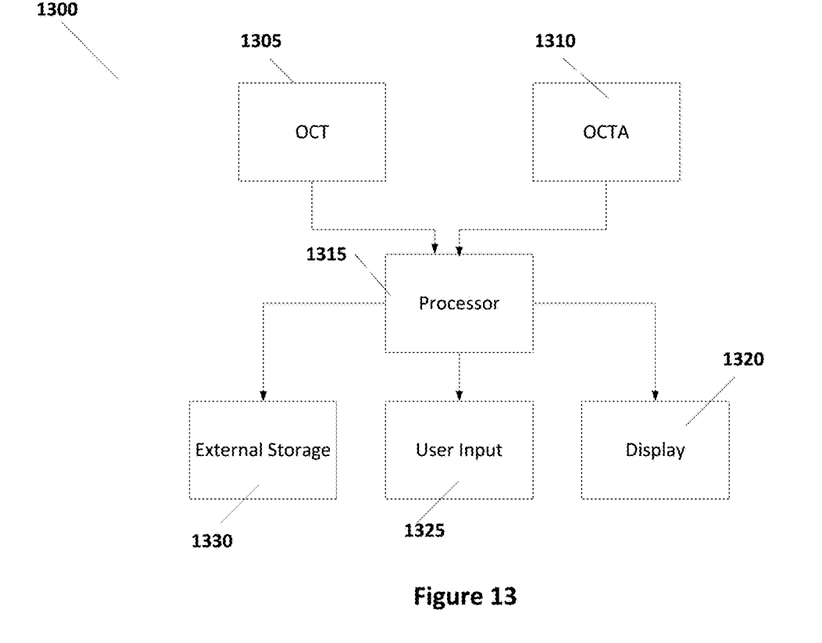
FIG. 13 illustrates an image processing system that can be used in the techniques illustrates in FIGS. 10, 11, and 12 according to some embodiments of the present invention.

FIG. 13 illustrates an image processor system 1300 according to some embodiments of the present invention. As show in FIG. 13, OCT data from an OCT imager 1305 and the OCTA data from an OCTA imager 1310 are input into a processor 1315. OCT imager 1305 and OCTA imager 1310 are discussed above. In some embodiments, OCT imager 1305 and OCTA imager 1310 may be combined into a single OCT imager where the OCTA data is derived from the 3D OCT data set by processor 1315.

Processor 1315 can be any processor, for example, a computer system with one or more processors, internal memory, and user interfaces. Internal memory can be any type and combination of volatile or non-volatile memory. The internal memory of processor 1315 may further include removable permanent storage devices such as CD ROM disc drives, solid-state memory hard drives, magnetic hard drives, or other device. Processor 1315 can manipulate and process data input from the OCT 1305 and OCTA 1310. In some embodiments, processor 1315 can further be coupled to a display 1320, user input devices 1325, and further external data storage 1330.

Processor 1315 can execute instructions stored internally in memory or read from an external storage medium to process data according to some embodiments. FIG. 10 illustrates an exemplary flow diagram 1000 illustrating instructions that may be executed by processor 1315 to form a vessel density map at different layers of retina structure 100 according to some embodiments. The results can be displayed on display 1320.

In step 1005 of diagram 100, 3D OCTA and OCT data sets are obtained from OCT 1305 and OCTA 1310, respectively, and input to processor 1315. In step 1010, segmentation is performed for at least one layer. For example, segmentation can be determined for the internal limiting membrane (ILM), inner plexiform layer (IPL), and retinal pigment epithelial (RPE) 108 boundaries represented in the OCT data set. In step 1015, pre-selected default settings can be used to identify and define the superficial, deep, avascular outer retina, and choroicapillary plexus in the OCT data step. Next, the OCTA image can be binarized in step 1020. In step 1025, the binarized OCTA image in step 1020 can be skeletonized. Binarization and Skeletonization of the OCTA image can be performed by any of the known techniques.

In step 1030 the neighborhood vessel features, such as width and length, can be compared to optimize the skeletonized vessel map of step 1025. In step 1035, the mean value of a pre-defined small region is calculated, the mean value to the centered pixel is assigned, and the calculation for each pixel in the entire OCTA image is produced. In step 1040, a color or other depiction mechanism is assigned for each pixel based on the value of each pixel. Finally, in step 1045 the color coded pixel is displayed to show a color coded vessel density map.

In some embodiments, using statistical significant population analysis and OCTA data from normal retina, a normative database can be created as a reference for patient data comparison. The method is similar to the analysis method commonly used with OCT retina thickness and nerve fiber thickness data as disclosed in the prior arts.

Figure 11:
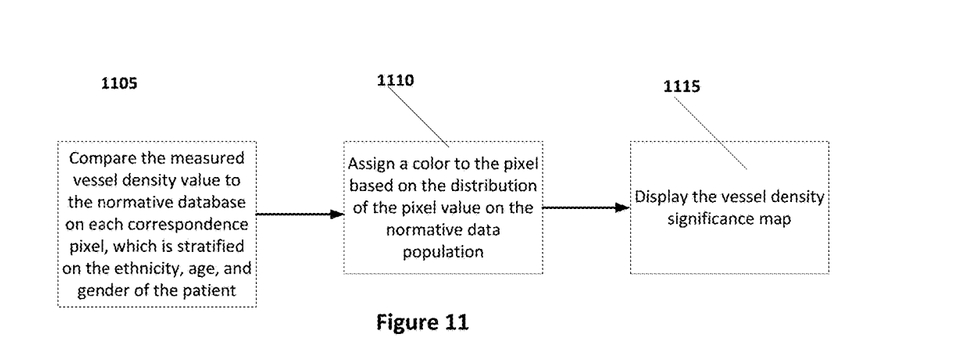
FIG. 11 shows a block diagram illustrating formation of a vessel density significance map according to some embodiments of the present invention.

According to some embodiments of the current invention, a normative database for vessel density, the normative vessel density database, on each enfaced OCTA vessel density map can be formed. FIG. 11 describes the steps to form a vessel density significance map. In step 1105 the measured vessel density value is compared to the normative database on each correspondence pixel. In some embodiments, the normative database can be stratified according to the ethnicity, age, and/or gender of the patient.

The statistical results can be color coded for easy visualization. In step 1110, a color is assigned to the pixel based on the distribution of the pixel value of the normative data population. For example, the pixel can be color coded as green when the value is within the normal range, yellow as the borderline, and red as out of normal range. The results can be displayed in step 1115 to display a density significance map.

In some embodiments, quantitative analyses can be performed on the OCTA enface image. For example, various measurements such as high flow (OCTA intensity or perfusion) area, low to no flow area including the fovea avascular zone (FAZ), vessel density, vessel length density, and flow index can be computed. Various image maps such as vessel density map and vessel length density map can be generated.

Computation of the High Flow Area

In some embodiments, a high flow area can be calculated on a binarized OCTA enface image. The binary image can be generated from OCTA image with, but not limited to, a user defined threshold. Any pixels with OCTA intensities greater than the threshold and within a region of interest (ROI) are considered and the area of these pixels is calculated as high flow area in some embodiments.

Computation of the Low to No Flow Area

In some embodiments, a seed point can be selected by a user or by an automated method from one of the pixels with very low intensities in the OCTA enface image. The input image is first binarized for vessel extraction where pixels are identified as vessels and non-vessels.

Next vessel extraction routine can be applied on the binary image. Connected vessel components with a length smaller than a predefined value can be discarded and considered as noise/non-vessels.

After the vessels are extracted, the non-vessel areas can be used to find the low to no flow area. A binary mask which indicates the location of the connected blob/area containing the seed point can be generated along with the size of the area.

Computation of Foveal Avascular Zone (FAZ)V

In some embodiments, a seed point can be selected by a user or by an automated method in one of the pixels with very low intensities within the foveal area (e.g. 1 mm diameter range from the foveal pit). The computation of FAZ can be calculated with the same steps disclosed above in the computation of the low to no flow area.

Computation of Vessel Density

The vessel density can be calculated as $$\text{Vessel density} = \frac{\int V dA}{\int dA},$$

where V is 1 when the OCTA pixel is considered vessel and 0 otherwise. A can be the total area or a pre-defined region-of-interest (ROI) area of the OCTA enface image.

Computation of Vessel Length Density

After skeletonization and post-filtering (e.g. pruning), vessels become single-pixel wide and the vessel length can be measured. The equation for calculating vessel length density is $$\text{Vessel length density}(mm^{-1}) = \frac{\int S(v) dL}{\int dA},$$

where S(V) is 1 for skeleton pixel and 0 otherwise. L is the pixel length and A can be the total area or pre-defined ROI area of the OCTA enface image.

Computation of Flow Index

The equation for calculating flow index can be given by:

$$\text{Flow index} = \frac{\int DV dA}{\int dA},$$

where V is 1 when the OCTA pixel is considered vessel and 0 otherwise. A can be the total area or a pre-defined ROI area of the OCTA enface image. D is the OCTA intensity value.

Generation of Vessel Density Map

The vessel density map can be generated by computing the vessel density from a pre-defined patch (e.g. 50 μm×50 μm) centered at each map pixel.

Generation of Vessel Length Density Map

The vessel length density map can be generated by computing the vessel length density from a pre-defined patch (e.g. 50 μm×50 μm) centered at each map pixel. In this detailed description, the term "vessel density" is used in general to include both the vessel density and vessel length density as described above.

Figure 12:
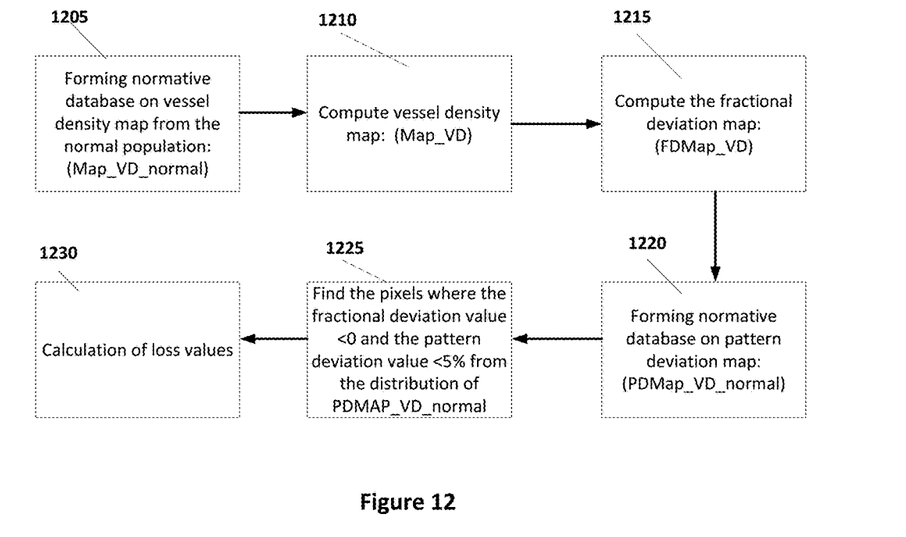
FIG. 12 shows a block diagram illustrating computation of the vessel density focal loss volume according to some embodiments of the present invention.

Finally, the loss of the capillaries can be calculated as focal loss as described in FIG. 12. The first step is to create a normative database on vessel density map from the normal population (Map_VD_normal) as in step 1205. Then, in step 1210, the patient's vessel density map (Map_VD) can be generated by calculating the expected or normal value at each pixel determined by the normative database (Map_VD_normal). In some embodiments, the expected value can be adjusted for age, gender, and/or ethnicity.

Next, in step 1215 the fractional deviation map (FDMap_VD) is computed. The map FDMap_VD represents the percent loss of vessel density at each pixel location. FDMap_VD is then created for each patient by comparing the computed vessel density value at each pixel in Map_VD to the normative database expected value in Map_VD_normal. This difference calculation is then divided by the expected normal value at each pixel to provide a percentage. This can be considered as the percentage loss if the computed value is less than the expected value from the database. Mathematically, it can be expressed by $$\text{FDMap\_VD}(p) = (\text{Map\_VD}(p) - \text{Mean}_{Map\_VD\_normal}(p))/\text{Mean}_{Map\_VD\_normal}(P),$$

where p is a map pixel and Mean the expected value at p from the normative database.

Next, a pattern map of vessel density (PMap_VD) can be generated. This map represents the normalized vessel density pattern of the vessel density map. It can be calculated by taking each pixel in the vessel density map and dividing by the average vessel density from the entire map according to some embodiments of the present invention. Thus a pixel that has the vessel density value the same as the average for the map will now have a value of 1. If the pixel value is less than the average value over the entire map, the normalized result will be a number less than 1, and vessel density values above the average would be above 1. This is done for the entire normative database to get a normal pattern map from the normative database (PMap_VD_normal) as in step 1220.

After that, a pattern deviation map of vessel density (PDMap_VD) is generated. In some embodiments, this map can be calculated by comparing a patient's individual pattern map (PMap_VD) to the expected pattern map from the normative database (PMap_VD_normal). At each pixel, the patient's pattern map value can be subtracted from the expected value of the pattern map from the normative database. Mathematically, it can be expressed by $$\text{PDMap\_VD}(p) = \text{PMap\_VD}(p) - \text{Mean}_{PMap\_VD\_normal}(p),$$

where p is a map pixel and Mean the expected value at p from the normative database.

The significance level at each data point is determined by comparing the value to the nonnative database (PDMap_VD_normal) as in step 1225. In some embodiments, a probability of 5% can be used to indicate statistical significance for example, although other values may be set. In step 1230, the fractional deviation values found in step 1225 can be summed and normalized by dividing by the map area to provide an indication of global loss values. Computations of loss values can be performed as indicated below.

Computation of Global Loss Volume of Vessel Density (GLV_VD)

The global loss volume of vessel density (GLV_VD) can then be computed. This value is based on the fractional deviation map (FDMap_VD) and is calculated in the following manner in some embodiments. It is the sum of the individual deviation values at each pixel where the FDMap_VD value is <0, and then divided by the total area to give an average percent loss of vessel density. In other words, the amount of deviation loss (below 0) at each pixel is summed, and then averaged over the number of pixels. Therefore, if every pixel has 15% vessel density loss on the FDMap_VD, then the GLV_VD will be 15%. If half of the pixel values have deviation loss of 15%, then GLV VD will be 7.5%.

Computation of Focal Loss Volume of Vessel Density (FLV_VD)

The focal loss volume of vessel density (FLV_VD) can provide useful clinical information. This value is based on both fractional deviation map (FDMap_VD) and pattern deviation map (PDMap_VD). In step 1230, it is calculated in the following manner in some embodiments. First, two deviation maps, FDMap_VD and PDMap_VD, are generated for the patient as described above. Then the FLV_VD value can be calculated by summing the fractional deviation map values at pixels where the fractional deviation value is below 0 and the pattern deviation map value is statistically significant (probability <5%). After summing the fractional deviation values at pixels where these two requirements are met, the result can then be divided by the total area.

While various aspects and embodiments have been disclosed herein, other aspects and embodiments will be apparent to those of ordinary skill in the art. The various aspects and embodiments disclosed herein are for purposes of illustration and are not intended to be limiting, with the true scope and spirit being indicated by the following claims. Those ordinarily skilled in the art will recognize, or be able to ascertain using no more than routine experimentation, many equivalents to the specific embodiments of the method and compositions described herein. Such equivalents are intended to be encompassed by the claims.

What is claimed is:

1. A method, comprising performing, by a computer system with one or more processors and memory, operations comprising:
    obtaining 3D Optical Coherence Tomography (OCT) data and 3D Optical Coherence Tomography Angiography (OCTA) data;
    performing segmentation for at least one boundary on the OCT data;
    processing the OCTA data with respect to the at least one segmented boundary from the OCT data to create an image representation by assigning an intensity value to each pixel of the image representation;
    assigning a binary value to each pixel of the image representation to form a binarized representation, the binary value indicating whether the pixel corresponds to a vessel;
    skeletonizing the binarized representation to form a skeletonized vessel map in which vessels are single-pixel wide;
    assigning a vessel density value to each pixel of the skeletonized vessel map to form a vessel density map, the vessel density value corresponding to a mean value of the binary values in a region around each pixel of the optimized skeletonized vessel map; and
    displaying the vessel density map.

2. The method of claim 1, wherein obtaining the 3D OCTA data includes generating the 3D OCTA data from the 3D OCT data provided by an OCT imager.

3. The method of claim 1, wherein performing segmentation includes segmenting of at least one layer to form an OCTA image.

4. The method of claim 3, wherein the at least one layer is chosen from a set consisting of an internal limiting membrane (ILM), an inner plexiform layer (IPL), and a retinal pigment epitherial (RPE).

5. The method of claim 3, further including computing a high flow area from the OCTA image.

6. The method of claim 3, further including computing a low flow area from the OCTA image.

7. The method of claim 3, further including computation of a foveal avascular zone from the OCTA image.

8. The method of claim 3, further including computation of an enface vessel density from the OCTA image.

9. The method of claim 8, further including calculating an enface vessel density map from the vessel density.

10. The method of claim 1, wherein processing the OCTA data comprises
    optimizing the skeletonized vessel map.

11. The method of claim 1, further including
    comparing the vessel density map with a normative database to form a vessel density significance map; and
    displaying the vessel density significance map.

12. The method of claim 11, wherein the normative database is stratified according to ethnicity, age, or gender.

13. The method of claim 1, wherein processing the OCTA data includes
    computing a fractional deviation from the vessel density map and a normative database;
    computing a pattern deviation map;
    analyzing the pattern deviation map to find fractional deviations; and
    determining a loss.

14. The method of claim 13, wherein determining a loss includes computation of a global loss volume.

15. The method of claim 13, wherein determining a loss includes computation of a focal loss volume.

16. An image processing system comprising a computer system with one or more processors and memory, the computer system being configured to:
    obtain 3D Optical Coherence Tomography (OCT) data and 3D Optical Coherence Tomography Angiography (OCTA) data;
    perform segmentation for at least one boundary on the OCT data;
    process the OCTA data with respect to the at least one segmented boundary from the OCT data to create an image representation by assigning an intensity value to each pixel of the image representation;
    assign a binary value to each pixel of the image representation to form a binarized representation, the binary value indicating whether the intensity value of the pixel exceeds a predetermined threshold;
    skeletonize the binarized representation to form a skeletonized vessel map in which vessels are single-pixel wide;
    assign a vessel density value to each pixel of the skeletonized vessel map to form a vessel density map, the vessel density value corresponding to a mean value of the binary values in a region around each pixel of the optimized skeletonized vessel map; and
    display the vessel density map.

17. The image processing system of claim 16, wherein processing the OCTA data comprises
    optimizing the skeletonized vessel map.

18. The image processing system of claim 16, wherein the computer system is further configured to:
    compare the vessel density map with a normative database to form a vessel density significance map; and
    display the vessel density significance map.

19. The image processing system of claim 18, wherein the normative database is stratified according to ethnicity, age, or gender.

* * * * *